United States Patent [19]

Urry

[11] Patent Number: 4,474,851
[45] Date of Patent: Oct. 2, 1984

[54] ELASTOMERIC COMPOSITE MATERIAL COMPRISING A POLYPEPTIDE

[75] Inventor: Dan W. Urry, Birmingham, Ala.

[73] Assignee: The University of Alabama in Birmingham, Birmingham, Ala.

[21] Appl. No.: 308,091

[22] Filed: Oct. 2, 1981

[51] Int. Cl.³ .............................................. B32B 15/00
[52] U.S. Cl. .................................. 428/373; 428/374; 428/394; 428/395
[58] Field of Search ............... 428/373, 374, 394, 395; 139/1 R; 3/1.4; 427/331

[56] References Cited

U.S. PATENT DOCUMENTS

| 3,982,543 | 9/1976 | Schmitt et al. | 428/394 |
| 4,132,746 | 1/1979 | Urry et al. | 3/1.4 |
| 4,187,852 | 2/1980 | Urry et al. | 128/334 |

Primary Examiner—Marion McCamish
Attorney, Agent, or Firm—Oblon, Fisher, Spivak, McClelland & Maier

[57] ABSTRACT

An elastomeric composite material formed from an artificial core fiber and an elastomeric polypeptide chemically bonded to the surface of the core fiber, where the polypeptide comprises tetrapeptide or pentapeptide repeating units or mixtures thereof, the repeating units comprise hydrophobic amino acid or glycine residues, and the amino acid residues of a given repeating unit exist in a conformation having a β-turn. Also disclosed are elastomeric fabrics formed from the elastomeric composite and the use of such fabrics in vascular prosthesis, as well as a method of forming such elastomeric composite materials.

12 Claims, 6 Drawing Figures

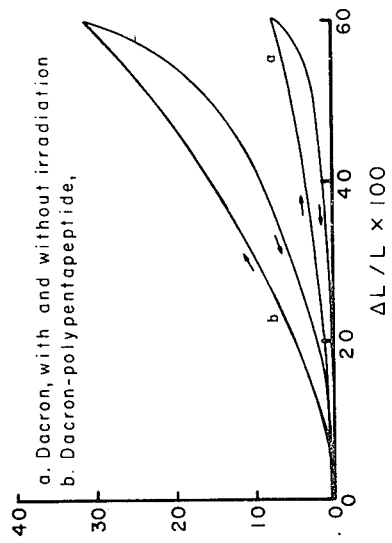
FIG. 3B
a. Dacron, with and without irradiation
b. Dacron-polypentapeptide,
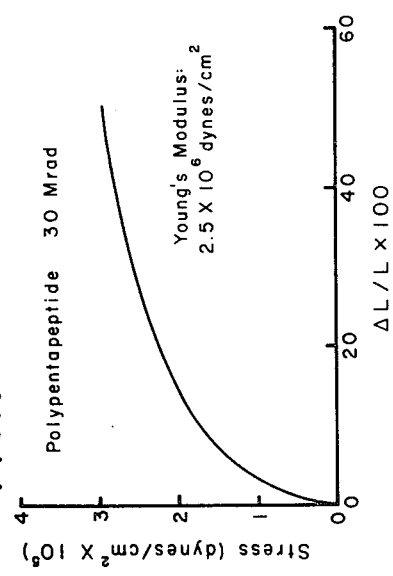
FIG. 3A
Polypentapeptide 30 Mrad
Young's Modulus: $2.5 \times 10^6$ dynes/cm$^2$
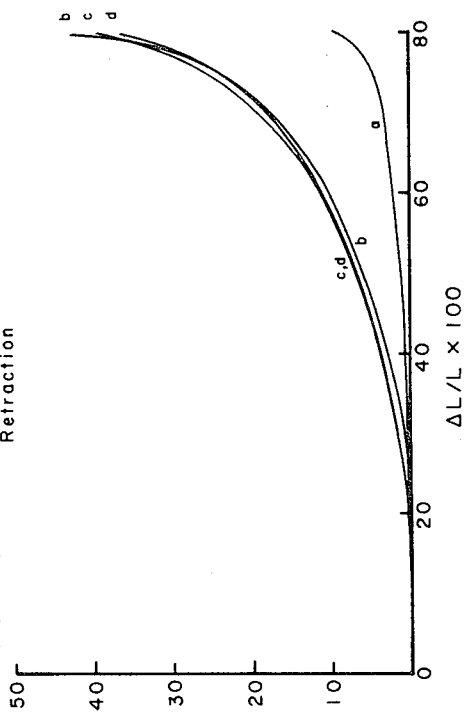
FIG. 3D Retraction
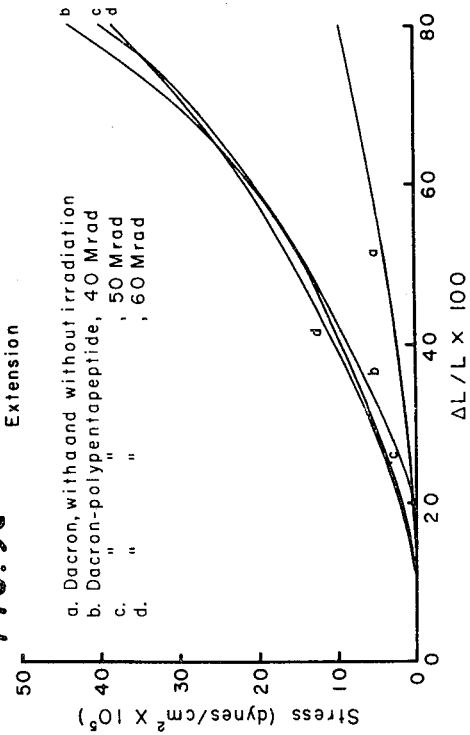
FIG. 3C Extension
a. Dacron, with and without irradiation
b. Dacron-polypentapeptide, 40 Mrad
c. "           "           , 50 Mrad
d. "           "           , 60 Mrad

DIRECTION OF STRETCH

ELASTOMERIC COMPOSITE MATERIAL COMPRISING A POLYPEPTIDE

This work was supported in part by the National Institutes of Health under Grant No. HL-11310.

BACKGROUND OF THE INVENTION

1. Field of the Invention

This invention relates to elastomeric fibers, to fabrics made from such fibers that are useful in cardiovascular prosthesis, and more particularly to an elastomeric composite material comprising an artificial core fiber and an elastomeric polypeptide chemically bonded to the surface of the core fiber or appropriately interwoven with it.

2. Description of the Prior Art

Replacement of a blood vessel by a posthetic device is an important and common practice in modern vascular surgery. Although some use is made of veins or arteries taken from other portions of a patient's body, most of such prosthetic devices are prepared from artificial materials that can be prepared in a variety of sizes and stored in a sterile state ready for use.

There are several essential properties of cardiovascular prosthetic materials, among which are the following:

1. Retardation of thrombosis and thromboembolism (antithrombogenic);
2. Minimal harm to blood cells and minimal blood cell adhesion;
3. Long life as prosthetic inserts; and
4. Close mimicry of the physical and chemical properties of natural blood vessel such as similar elastic modulus and tensile strength.

Another useful property would be a chemotaxis that induced rapid endothelialization and invasion of connective tissue cells for vascular wall reconstruction in a manner such that the prosthesis would be slowly replaced by and integrated into newly synthesized internal elastic lamina. None of the materials presently being used can fulfill all of these requirements.

The most commonly used fabric for blood vessel prosthesis is made from Dacron (Trademark, DuPont), a synthetic polyester fiber made from polyethylene terephthalate. Dacron has been used in several weaves and in combination with other materials. An example of a frequently used material is the DeBakey Elastic Dacron fabric manufactured by USCI, a division of C. R. Bard, Inc. (Cat. No. 007830). Other commonly used materials are felted polyurethane and polytetrafluoroethylene (Berkowitz et al., Surgery, 72, 221 (1972); Wagner et al., J. Surg. Res., 1, 53 (1956); Goldfarb et al., Trans. Am. Soc. Art. Int. Org., XXIII, 268 (1977)).

However, none of these materials, even when specially woven or crimped, mimics the elastic nature of natural blood vessel walls (Takabayashi et al., J. Surg. Res., 19, 209 (1975)). Because of this, blood pressure response and blood flow occur differently in natural and artificial blood vessels, and the desirable normal flow characteristics and pressure response are not attained. Changes in blood flow are undesirable and often lead to clotting. A material that more closely mimics the natural elastic behavior of blood vessels is still needed.

SUMMARY OF THE INVENTION

Accordingly, it is an object of this invention to provide an artificial material having elastic character such that a blood vessel prosthesis produced from such a material would mimic the pressure response characteristics of natural blood vessels.

It is a further object of this invention to provide an artificial material suitable for blood prosthesis having chemical properties that closely resemble the chemical properties of natural blood vessel elastic lamina.

These and other objects of this invention as will hereinafter become more readily apparent have been attained by providing an elastomeric composite material, comprising an artificial core fiber, and an elastomeric polypeptide chemically bonded to the surface of said core fiber, wherein said polypeptide comprises tetrapeptide or pentapeptide repeating units or mixtures thereof, wherein said repeating units comprise amino acid residues selected from the group consisting of hydrophobic amino acid and glycine residues, and wherein said repeating units exist in a conformation having a $\beta$-turn.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings and photomicrographs, wherein:

FIG. 3 shows stress-strain curves for a polypentapeptide/Dacron composite fabric, for the cross-linked polypentapeptide itself, and for Dacron alone;

DESCRIPTION OF THE PREFERRED EMBODIMENTS

Figure 1:
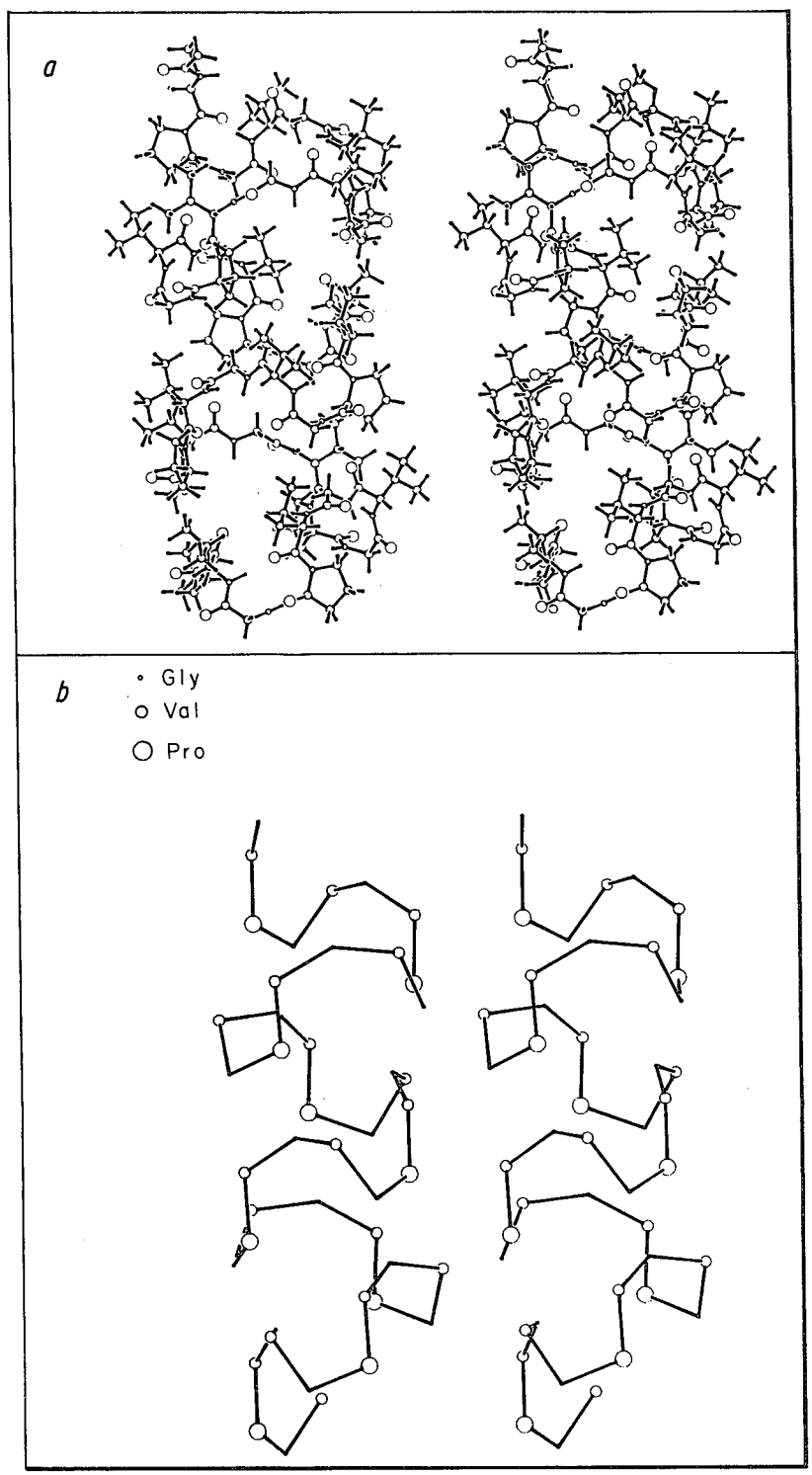
FIG. 1 shows a series of computer-generated stereoscopic drawings of a $\beta$-spiral structure of a polypentapeptide of the present invention.

The present invention arose as the result of investigations into the structure of elastic fibers present in blood vessel walls and other elastic fibers present in humans and animals. The connective tissue of vascular walls is formed from two principal types of protein. Collagen, the principal proteinaceous component of connective tissue, forms the strength-giving structure. In the vascular wall, and particularly in its internal elastic lamina, collagen is associated with natural elastic fibers formed from a different protein. In the relaxed wall the collagen fibers tend to be folded or crimped, and the elastic fibers are in their retracted state. On distension or stretching, the elastic fibers stretch out, and, as their extension limit is approached, the collagen fibers come into tension to bear the load. As the load diminishes, the elastic fibers draw the wall back to its original dimensions and the collagen fibers back into their folded state. In a synthetic vascular material of the types currently available, such as Dacron, the weave can be viewed as providing the structural analogue of folded collagen, but there is no true elastomeric component.

The central portion of the elastic fibers of vascular wall, skin, lung and ligament is derived from a single protein called tropoelastin. Polypeptide sequences of tropoelastin form vascular wall have been shown by Sandberg and colleagues to contain a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$, where Ala, Pro, Val, and Gly respectively represent alanine, proline, valine, and glycine amino acid residues. (Peptide representations in this application conform to the standard practice of writing the $NH_2$-terminal amino acid residue at the left of the formula and the $CO_2H$-terminal amino acid residue at the right). A high polymer of the hexapeptide has been synthesized, whereby it forms cellophane-like sheets. The hexapeptide is therefore thought to fill a structural role in the natural material. Synthetic high polymers of the pentapeptide and of the tetrapeptide, on the other hand, are elastomeric when cross-linked and appear to contribute to the functional role of the elastic fiber. For example, the chemically cross-linked polypentapeptide can, depending on its water content, exhibit the same elastic modulus as native aortic elastin.

Investigations into the structure of the natural polypentapeptide (PPP) and polytetrapeptide (PTP) have disclosed several features in common and have led to the present invention by uncovering the essential features responsible for the elasticity of these molecules. Now that these features have been discovered, it is possible to predict which other polypeptides will exhibit elasticity, thereby making possible the synthesis of a new class of elastomeric materials. Of course, it is likely that not all elastic polypeptides function in the way described herein or have the same structural features. Other modes of action responsible for elasticity are likely to exist in molecules of different structure and, if so, may have no resemblance to the elastomeric molecules described herein.

An essential feature of the elastomeric PPP and PTP of the invention is the existence of a sequence of regularly appearing $\beta$-turns in the protein's secondary structure, i.e., the conformation of its peptide chain. A $\beta$-turn is characterized by a ten atom hydrogen bonded ring of the following formula:

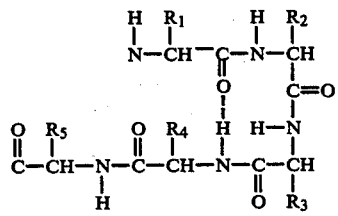

In this formula, $R_1$–$R_5$ represent the side groups of the respective amino acid residues.

Stereoscopic views of a PPP of the invention are shown in FIG. 1, which shows a series of $\beta$-turns repeating in a regular sequence, one $\beta$-turn for each pentapeptide repeating unit. In these views the overall conformation of the peptide chain is a $\beta$-spiral, i.e., a series of regularly repeating $\beta$-turns. The form of the $\beta$-spiral is best seen in FIG. 1A, in which the position of each amino acid is represented by a dot. FIG. B shows the structure and conformation of each amino acid in the $\beta$-spiral by showing the position of each atom in the PPP. It can be seen from these stereoscopic views that the spiral structures are more open than the more common $\alpha$-helix. As a result, the atoms between the atoms that participate in hydrogen bonding have a relatively great freedom of movement, more so than in an $\alpha$-helix. This is particularly true of librational motions involving peptide moieties. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and the amino hydrogen of the peptide bond not be involved in hydrogen bonding to other parts of the molecule or to other molecules. Otherwise a greater energy barrier to the libration exists and motion will be restricted. Since non-hydrogen-bonded segments having freedom of motion exist in the $\beta$-spiral between the points of hydrogen bonding for the $\beta$-turns, these segments may be said to be librationally suspended. Librationally suspended segments therefore are a structural feature that exists in the PPP because of the repeating $\beta$-turns with relative infrequent hydrogen bonding. Librationally suspended segments resulting from the $\beta$-spiral structure and other features still to be discussed are important features that are thought to give rise to elasticity, as will be further discussed.

Another factor leading to the high librational freedom of such molecules is the absence of polar interactions between the amino acid residues, either intrachain or interchain, other than the previously mentioned hydrogen bond. The amino acid residues present are all hydrophobic or glycine and accordingly do not exert significant forces on one another through space. If charged or polar groups were present, electrostatic interactions would limit librational freedom and restrict the number of available states in the relaxed (non-extended) form of the molecules. Polar and charged amino acid residues are not strictly prohibited, however, if their presence does not destroy the elasticity of the polypeptide molecule as a whole. For example, an occasional serine residue is present in naturally occurring tropoelastin without destroying elasticity. Accordingly, hydrophobic amino acid residues and glycines are preferred in forming elastomeric polypeptides of the present type although other amino acids may be present to a small extent.

The size of the repeating unit is important in determining the stability and dynamic properties of the $\beta$-spiral. Repeating units having fewer than four or more than five amino acid residues do not easily form $\beta$-spirals having the required librational motions. Three amino acid residues are too few for an efficient $\beta$-turn and six residues result in suspended segments so long that other conformations become energetically more stable. Thus, elastomers of the present type appear to be limited to polypeptides having tetrapeptide or pentapeptide repeating units.

The choice of individual amino acids from which to synthesize the repeating units and resulting polypeptide is unrestricted so long as the resulting structure comprises librationally suspended segments in a $\beta$-spiral. The amino acids are not restricted to $\alpha$-amino acids, although these are preferred, since it has recently become possible to predict the occurrence of $\beta$-turns from the $\alpha$-amino acid sequence of a polypeptide. A review article discussing the prediction of protein conformation, including the prediction of $\beta$-turns, was recently published by Chou and Fasman, Ann. Rev. Biochem., 47, 251 (1978), which is herein incorporated by reference. In addition, it appears from the studies leading to the present invention that preferred side chains of the amino acids are hydrogen or hydrocarbon chains having 1–4 carbon atoms. Examples are the naturally occuring amino acids glycine, alanine, valine, leucine, and isoleucine as well as closely related molecules such as 2-methyl-2-aminopropanoic acid, 2-aminobutanoic acid, and 2-methyl-2-aminobutanoic acid, although it is preferred that the α-carbon have an α-hydrogen. Proline is also a preferred amino acid. Where amino acids having chiral centers at the α-carbon occur in the natural PTP and PPP, it is preferred that these amino acids have the same relative configuration in order that the β-turns will occur.

Given positions of the repeating units have amino acid residues that are particularly preferred. The first amino acid residue is preferred to be valine, leucine, or isoleucine; the second is preferred to be proline; the third is preferred to be glycine; and the fourth is preferred to be glycine or tryptophan for the tetrapeptide and valine, leucine or isoleucine for the pentapeptide. If the repeating unit is a pentapeptide, the fifth residue is preferred to be glycine. Particularly preferred repeating units are Val-Pro-Gly-Gly and Val-Pro-Gly-Val-Gly.

Although Applicant does not wish to be bound or limited to the following theory, it appears that the elasticity of polypeptides of the structure discussed above is caused by thermodynamic drive toward greater entropy. The relaxed state of the β-spiral has a large degree of librational freedom and thus the atoms of the peptide chain can exist in a large number of positions. When the molecules are stretched, the degree of freedom is reduced, particularly for librational motions, and when the tension is released, a thermodynamic driving force toward higher entropy results in reformation of the contracted β-spiral.

A major limitation of the polypentapeptide and polytetrapeptide, even when cross-linked, is that, while elastomeric, these materials are lacking in strength. The limited strength of the synthetic matrices is not unlike the biological situation, as the role of the elastic fibers is not one of load bearing but rather of providing resistance to extension, and of reforming the original tissue configuration when tension is released. Thus, in addition to an elastomeric component of the correct elastic modulus, what was needed in order to develop, for example, a prosthetic vascular wall material, was a collagen-like load bearing component. This has been achieved by compounding the synthetic elastomeric high polymers of the polytetrapeptide and polypentapeptide described above to a second material with greater strength. The second material forms the core of the composite fiber and will be referred to as the "collagen analogue" or "core fiber". The term core fiber is not limited to those forms of elastomeric composite materials in which a first fiber is coated with a second material, but also refers to other forms in which a strength giving fiber (the core fiber) is chemically bonded to a second component that is elastomeric (the polypeptide). For example, elastomeric polypeptide fibers may form strands between the segments of a crimped core fiber. The essential feature is that a chemical bond (of any type) exists between the surface of the core fiber and the elastomeric polypeptide so that the two components do not become separated while the elastomeric component is being stretched or is reforming the related β-spiral. The chemical bond may be covalent or ionic bonding, hydrogen bonding, or the result of electrostatic interactions of various types, such as ion-dipole and dipole-dipole interactions. Covalent bonding is preferred. Linkages may be formed in any conventional manner and, if covalent bonds are to be formed, they can be accomplished by reacting a functional group of the polypeptide with a functional group of the core fiber. The functional groups may be present naturally as part of the polypeptide or core fiber or may be formed later, for example, by suitable chemical reactions involving the already formed core fiber or polypeptide. Such chemical reactions are well known and are discussed in more detail later in connection with cross-linking of the polypeptide.

The collagen analogue may be any fiber-forming artificial material having a tensile strength of 10 to 50 kg/mm$^2$, preferably about 20 to 40 kg/mm$^2$, and most preferably about 30 kg/mm$^2$ and an elastic modulus of no more than $5 \times 10^{10}$ dynes/cm$^2$ at 5% extension, preferably no more than about $1 \times 10^{10}$ dynes/cm$^2$, that is biologically compatible with use in a living organism. By biologically compatible is meant that the core polymer, when compounded into the final product with the elastomer, will not harm the organism in which it is implanted to such a degree that implantation is as harmful as or more harmful than the needed vascular replacement. The term artificial fiber as used herein refers both to fibers formed from synthetic materials and to fibers formed from naturally occurring materials. The term artificial refers to the act of forming the fiber rather than the act of forming the material out of which the fiber is made. If use outside the living body of an organism is anticipated, biological compatability is not required. Examples of suitable types of polymers which can form fibers of the required properties include polyamides, polyesters, polyvinyls, polyethylenes, polyurethanes, polyethers, and polyimides. Non-polymeric fibers, such as metal fibers, and inorganic fibers, such as glass, may be of use in some applications, although their use is less preferred.

Suitable polyamides include polyamino acids, such as poly condensation products of p-aminobenzoic acid, and condensation products of diamines with dicarboxylic acids, such as hexamethylenediamine and terephthalic acid. Another suitable polyamide would be direct synthesis of an artificial collagen modelled after natural collagen. Polyesters suitable for use with the invention include polyhydroxy acids and condensation products of diols or polyols with dicarboxylic acids, such as ethylene glycol and an aromatic dicarboxylic acid. Examples of polyvinyls include polymethyl methacrylate and other esters of acrylic and methacrylic acid, polyvinyl alcohol, and esters of polyvinyl alcohol. Polyethylenes include polyethylene itself and halogenated derivatives of polyethylenes, such as polyvinyl chloride, as well as perhalogenated polyethylene, such as polytetrafluoroethylene. Polyurethanes include addition products of aromatic, aliphatic, or araliphatic diisocyanates with either diamines or diols. Polyethers include epoxy resins such as poly(propylenoxide) and poly(ethylene oxide). Polyimides include polymers derived from pyromellitic dianhydride and aromatic or aliphatic diamines.

Preferred collagen analogues are polyesters. Preferred polyesters are condensations products of phthalic, isophthalic, or terephthalic acid and diols, of which the most preferred are polymers derived from terephthalic acid and a 1,2-diol, such as, for example, the condensation product of terephthalic acid and ethylene glycol that is sold under the trademark of Dacron by E. I. duPont deNemours and Co. Polyesters having aromatic nuclei, such as Dacron, can be easily derivatized in order to provide function groups for covalent attachment of the polypeptide. For example, formylation and carboxylation of aromatic rings are easily carried-out, well-known reactions and provide functional groups that will react with amino groups present in the polypeptide.

The polymers listed above or other suitable materials are synthesized according to standard techniques and formed into fibers or fabrics, or are obtained from commercial sources as fibers or fabrics or in a form that may be manufactured into fibers or fabrics. Methods of preparing such fibers are well known and are not considered to be part of the present invention. The list given above is not intended to be limiting and any fiber or fabric that meets the standards of strength and biocompatability previously given may be used, whether known at the time of this application or discovered later. A crimping of the core fiber that will provide a uniform extendability of 200% or more is desirable. If the fiber is formed into a fabric, this crimping may be accomplished by the fabric weaving process. Crimping and expandable weaves are well known and are not considered to be part of the essence of the invention.

The diameter of the core fiber is not limited and may be varied as needed for the intended application. When the fiber is to be used in the formation of a vascular prosthesis, a diameter of less than 20 μm will give satisfactory results. Fibers with finer diameters will have a greater surface area per unit weight and are therefore preferred in order to allow better attachment of the elastomeric material to the surface of the collagen analogue (core fiber) and a more effective refolding of the collagen analogue. Diameters of less than 2 μm are preferred with a diameter of about 1 μm being most preferred.

Synthesis of the polypeptide elastomers is straightforward and easily accomplished by a protein chemist. The resulting polypeptides have the structure X-(repeating unit)$_n$-Y where X and Y represent any chemically compatible end group on the amino and carboxyl ends of the molecule, respectively, and n is an integer equal to or greater than 40. Particularly preferred are polypeptides having molecular weights greater than 10,000 daltons. It is possible that one or more amino acid residue or segment of amino acid residues may be interspersed within the polypeptide chain so long as the elasticity of the resulting molecule is not completely disrupted.

Examples of terminal X and Y end groups include the repeating peptide units themselves with free amino or carboxylic acid groups or salts thereof and peptide or amino acid units that have retained a blocking group that was present during synthesis of the polypeptide or that have a blocking group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the β-turn conformation of the polypeptide or confer bio-incompatibility to the molecule as a whole.

Methods of preparing polytetrapeptide and polypentapeptide polymers of this invention have been disclosed in Rapaka and Urry, Int. J. Peptide Protein Res., 11, 97 (1978), Urry et al, Biochemistry, 13, 609 (1974), and Urry et al, J. Mol. Biol., 96 101 (1975), which are herein incorporated by reference. The synthesis of these peptides is not considered to be a part of the present invention, which is directed to an elastomeric composite fiber, of which the peptides are one component. The following summary, which is not to be considered limiting, is an example of one general method of synthesizing the polypeptides. This summary is directed to synthesis of a polytetrapeptide, but synthesis of a polypentapeptide would be carried out in a like manner.

The first step in the formation of the polytetrapeptide is synthesis of a tetrapeptide monomer. An amino-protected amino acid is allowed to react with a carboxylate-protected amino acid so that an amide link is formed between the respective free carboxylate and amino groups. This might give, for example, Boc-Val-Pro-OMe, where Boc is a t-butyloxycarbonyl protecting group and OMe represents the methyl ester of the proline residue. One of the protecting groups is removed (in this case the methyl ester group by base hydrolysis), and the resulting dimer containing a reactive terminal functional group is reacted with a second dimer formed in like manner but having the other protective group removed (in this case H-Gly-Gly-OMe formed by acid hydrolysis of Boc-Gly-Gly-OMe). The resulting protected tetramer (Boc-Val-Pro-Gly-Gly-OMe) is converted into the reactive monomer by, for example, removal of the Boc protecting group and replacement of the methyl ester with the p-nitrophenyl ester. The resulting reactive monomer is polymerized, in the presence of a catalyst such as triethylamine if necessary, to give the polypeptide. A blocking group, such as H-Val-OMe may be added at the conclusion of the polymerization reaction to convert the remaining reactive p-nitrophenyl esters to non-reactive terminal groups if desired.

When a modified chemical structure is desired, as, for example, when chemical cross-linking will be carried out, side-group-blocked lysine or glutamic acid (or another amino acid with a protected side group capable of forming a cross-link after the protecting group is removed) may be utilized in place of one of the normal amino acids that is present in the polypeptide chain. A synthesis of a chemically cross-linked polypentapeptide is disclosed in U.S. Pat. No. 4,187,852, which is herein incorporated by reference.

The weight ratio of the core fiber to the sheath component can vary as required for the intended use, with a ratio of from 10:1 to 1:10 being preferred, with from 1:1 to 3:10 being most preferred, when the composite fiber is to be used in a prothesis for a major artery. Lesser amounts of the elastomeric component, preferably about a 1:1 ratio, is preferred for a small artery prosthesis.

The two components are brought together in any manner that results in the formation of a synthetic composite fiber in which the high strength polymeric fiber forms a core which is surrounded by a sheath of the polypeptide. It is desirable to have the elastomeric component bridge between folds in the collogen analogue. In general, this can be accomplished by coating a preformed, crimped polymeric fiber or woven fabric with a solution suspension, or coacervate of the polypeptide, although it may be possible to spin or otherwise form the core fiber in a solution or suspension of the polypeptide.

A preferred method of forming the composite takes advantage of the property of coacervation exhibited by both the polypentapeptide (PPP) and the polytetrapeptide (PTP). The PPP and PTP are soluble in water at 20° C. but on raising the temperature above 30° C. the polymers associate and settle to form a dense, sticky phase called the coacervate. The process is entirely reversible, though dissolution can be slow. In order to impregnate the collagen analogue in preparation for compounding, fibers or strips of fabric made from the collagen analogue can be placed on the bottom of a chamber of like dimension. It is preferred to use a polytetrafluoroethylene chamber since the coacervates do not adhere well to polytetrafluoroethylene. Aqueous solutions containing PTP or PPP are added to each chamber covering the fabric. The temperature is raised and the coacervate allowed to settle onto the surface of the fiber or into the weave of the fabric. If a fabric is used, it is preferred to largely fill the spaces between the fibers of the fabric. The supernatant can be either removed or allowed to dry down to the level of the fabric strip. The PPP or PTP impregnated strip or fibers are then removed from the chambers.

Other examples of methods of depositing the polypeptide on the surface of the core fiber include evaporation of solutions of the polypeptide on the surface of the fiber and reacting the polypeptide with functional groups present in the core fiber while the core fiber is suspended in a solution of the polypeptide.

Once the polypeptide become chemically bound to the core fiber, it is generally desirable to cross-link the molecules of the polypeptide. The method of creating the linkage is not limited to the methods disclosed in this application and may be any method of covalent or non-covalent linkage that does not prevent the composite fiber from behaving as an elastomer. Suitable methods and types of linkages include cross-linking with ionizing irradiation and chemical modification or substitution of amino acid residues of the peptide repeating units and of the collagen analogue repeating units in order to form reactive side groups that undergo chemical reaction with each other (chemical cross-linking), e.g., by amide linkage, aldol condensation, Schiff base formation, enzymatic cross-linking by lysyloxidase, or ester formation. Another suitable method of cross-linking comprises the use of photoactivatable agents such as those giving rise to ertsenes or nitrenes which may be attached as amino acid side groups or introduced as separate adjustable molecules.

A preferred type of chemical cross-linking occurs when polypeptides are prepared in which some of the repeating units are replaced by units in which one of the amino acid residues is replaced by the residue of an amino acid that has a reactive side chain. Preferred is preparation of a first batch of polypeptide in which a residue of some of the repeating units is replaced by an amino dicarboxylic acid, such as aspartic or glutamic acid, and a second batch of polypeptide in which a residue of some of the repeating units is replaced by a diamino carboxylic acid, such as lysine or ornithine. After a mixture of these two batches has been formed into a sheath around the core fiber, the free amino and carboxylic acid side group are allowed to react to create the cross-linkages. Formation of cross-linked PPP produced in this manner but in the absence of the core fiber is described in U.S. Pat. No. 4,187,852, which is herein incorporated by reference. If chemical cross-linking is used, it is also necessary to provide reactive functional group in the core fiber so that linkages between the peptide elastomer and the core fiber will also occur. Such modifications are well understood by polymer chemists and may include, for example, glycidyl esters of acrylates or methyacrylates (as examples of reactive groups present during formation of the core polymer), or amino or carboxylic acid groups added to the terephthalic acid moeity of Dacron (as examples of reactive groups formed after formation of the core fiber).

The degree of cross-linking is not critical so long as elastomeric properties are imparted to the resulting composite fiber and can be varied to provide the desired dynamic mechanical properties. Preferred is an average of one cross-link for every 10 to 100 pentamer or tetramer repeating units with 20 to 50 being most preferred. The degre of chemical cross-linking can be controlled by selecting the proper proportions of reagents. In general, the ratio of repeating units with reactive side groups to unmodified repeating units within a single molecule can vary from 1:1 to 1:10 with a ratio of about 1:3 being preferred. When two batches of polypeptide containing carboxylate or amino side groups as described above are used, the ratio of carboxylate-side-group-containing polypeptide to amino-side-group-containing polypeptide can vary from 4:1 to 1:4 with a ratio of about 1:1 being preferred.

When irradiation cross-linking is performed, a satisfactory approach is irradiation with gamma radiation from a cobalt-60 source. Other radiation energies required to provide a cross-linking action without excessive destruction of the core fiber or elastomeric peptide structure may be easily determined by simple experimentation. The degree of cross-linking is determined by the length of time and energy of the irradiation when irradiation cross-linking is performed. At least two cross-linkages per molecule are needed. The number of cross-linkages per molecule and the elastic modulus increase as the radiation dose increases. The requisite time for any desired amount of cross-linking is easily determined by simple experimentation for any given source of irradiation energy. Samples of non-cross-linked composite fiber are exposed to the source of ionizing energy for varying lengths of time, and the resulting elastic modulus is measured. In this manner the irradiation time required to produce an elastic modulus necessary to match a specific design characteristic of the composite fiber can easily be determined. For use in forming vascular wall prosthetic devices, an elastic (Young's) modulus of $10^6$ to $10^7$ dynes/cm$^2$, preferably about $4 \times 10^6$ dynes/cm$^2$, for the cross-linked composite fiber is desirable. This is approximately the elastic modulus of the vascular wall.

The elastomeric composite fibers may be woven into a fabric or an elastomeric fabric may be formed from a fabric of the core fiber material by coating and cross-linking the polypeptide on the surface of the fibers of the preformed fabric. When the resulting fabric has an elastic modulus of from $10^6$ to $10^7$ dynes/cm$^2$ and has been formed into an appropriate shape, for example, a tubular shape, the resulting article may be used in vascular prosthesis. One simple way to obtain the desired tubular form, not considered to be limiting, would be to place the preformed woven and crimped tube of core fiber material between two concentric glass tubes with the outer tube containing an aqueous solution of PTP or PPP. The temperature of the solution would then be raised to allow coacervation to take place and the resulting impregnated woven fabric composition would be cross-linked by γ-irradiation at an appropriate dose.

It is also possible to form separate strength-giving and elastomeric fibers and to interweave them into a fabric of the desired shape. The first fiber, which is essentially non-elastic, would provide strength while the elastomeric polypeptide fiber would provide elasticity.

Once the synthetic composition material has been formed into an appropriate shape, if it is intended for use as a vascular replacement or patch, it is surgically inserted into a human or animal in place of diseased or missing vascular material. Tubular material may be used to replace an entire vein or artery by attaching each end to the distal and proximal free ends of a blood vessel having a missing or surgically removed section. Attachment is made so that blood flows through the tube without major leaking by any means capable of providing medically acceptable attachment, such as suturing or cauterizing. The elastomeric composite may be made in the form of a patch to be attached by the same methods if replacement of only a portion of a blood vessel is desired. Also tubular material may be used as a lining to replace diseased tunic intima following endorterectomy.

The above disclosure generally describes the present invention. A more complete understanding can be obtained by reference to the following specific examples, which are provided herein for purposes of illustration only and are not intended to be limiting unless otherwise specified.

EXAMPLE 1

Polytetrapeptide/Dacron Composite Material

The polytetrapeptide H(Val-Pro-Gly-Gly)$_n$Val-OMe was synthesized as previously reported in Rapaka and Urry, Int. J. Pept. Protein Res., 11, 97 (1978), with n>>40.

For the cross-linking of the polytetrapeptide alone, concentrated aqueous solution (40 mg peptide in 60 μl of H$_2$O) were placed in small tubes with 4.4 mm ID which were irradiated at 30 MRADs. Twenty-four cobalt sources, each ten inches long, three-fourths inch wide and one-eighth inch thick, were positioned in three concentric circles of four, six and eight inches diameter. Eight sources were equally spaced on the circumference of each circle. The radiation intensity was measured to be 13,317 roentgen per minute. The samples were placed in the center of the source configuration for various times so that the radiation absorbed dosages (RADs) could be varied from 30 to 100×10$^6$.

For compounding, coacervation of the polytetrapeptide (PTP) was carried out in a chamber with strips (7 mm×25 mm) of DeBakey Elastic Dacron Fabric (USCI, a division of C. R. Bard, Inc., cat. No. 007830) on the bottom. As the temperature was raised the aqueous solution of the PTP began to coacervate, i.e. to aggregate, to form more dense PTP clusters which settled into the Dacron weave extensively filling the spaces within the fabric. The Dacron strips, impregnated with the PTP coacervate, were sealed in 2.5 cm×2.5 cm glass slides with a 0.5 mm thick teflon spacer between the glass windows. The glass slides were then placed in the radiation chamber for periods resulting in 50, 75 and 100 MRAD doses.

The stress-strain apparatus used to record the data was designed and built in the inventors' laboratory. A rigidly mounted Statham model UC-2 transducing cell with UL4-0.5 load cell accessory was used to record force data. Using the required excitation and signal conditioning circuits the output of the UC-2 transducer was recorded on the y-axis of an x-y recorder. The sample was elongated at a constant rate of 2 mm/minute using a Velmex model B2509CJ Unislide driven by a variable speed motor through a Metron Instruments speed reducer. The position of the moving holder was recorded on the x-axis of the x-y recorder using a BLH linear displacement transducer and appropriate excitation and signal conditioning circuits. The thickness and the width of the sample were measured before being placed in the clamps. One clamp was attached to the UC-2 transducer and the other to the moving platform. Initial lengths ($L_i$) of 0.5 and 0.76 cm were used. The x-axis scale is $\Delta L/L_i$ where $\Delta L$ is the displacement of the moving end of the sample from $L_i$. The cross-section area was used to calculate dynes/cm$^2$ from the recorded force.

It was found that 30 MRADs caused the polytetrapeptide coacervate itself to become a rubbery hemisphere which could be removed from the rounded bottom of the tube intact. Irradiation cross-linking of the coacervate impregnated Dacron at 75 MRADs and 100 MRADs resulted in a material with decreased strength and with no significant elastomeric properties. Irradiation of the PTP-Dacron system at 50 MRADs gave rise to a material with the stress-strain properties seen in FIG. 2.

Figure 2:
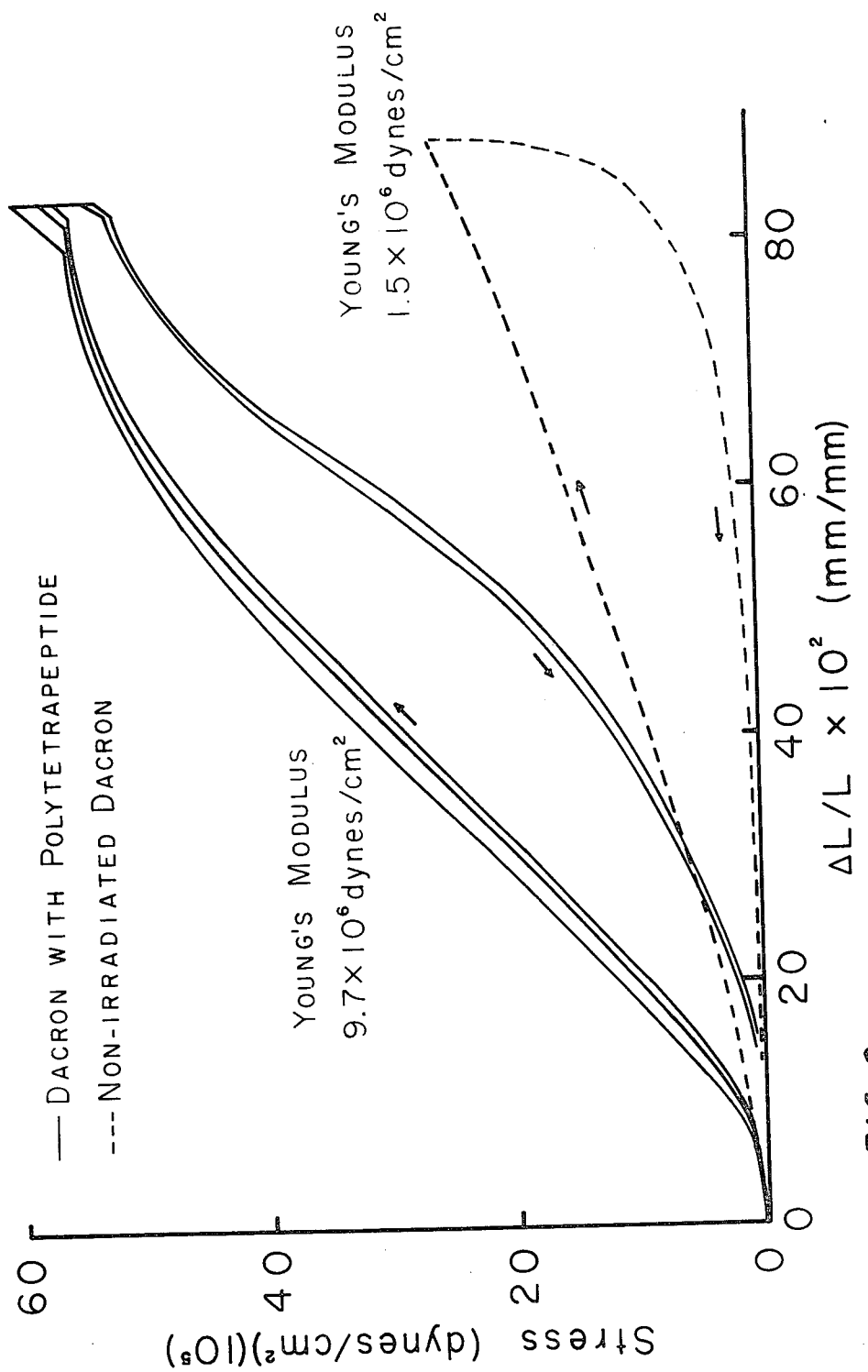
FIG. 2 shows stress-strain curves for a polytetrapeptide/Dacron composite fabric and for the Dacron material (collagen analogue) itself.

Also included in FIG. 2 is the stress-strain curve for the Dacron knit without PTP where the slope on stretching gives rise to an apparent Youngs modulus of 1.5×10$^6$ dynes/cm$^2$ but there is no significant elastomeric retraction. In contrast, the cyclical stress-strain curves of 50 MRAD-PTP-Dacron knit exhibit reproducible sigmoid curves both on stretching and on retraction with a hysteresis lag on retraction (see FIG. 2). While the sigmoid curves as shown in FIG. 2 were consistently observed in some experiments, curves of the form shown in FIG. 3 were also commonly found for the polytetrapeptide. Near 80% extension a stiffer component is seen to come into tension which could be due to Dacron fibers beginning to bear the load. The Youngs (elastic) modulus at 33% elongation of the compounded PTP-Dacron is 9.7×10$^6$ dynes/cm$^2$, approximately three times greater than observed for isolated fibrous elastin.

EXAMPLE 2

Polypentapeptide/Dacron Composite Material

The high polymer of the pentapeptide (Val-Pro-Gly-Val-Gly)$_n$ was synthesized as described Urry et al, Biochemistry, 13, 609 (1974) and Urry et al, J. Mol. Biol., 96, 101 (1975). The polypentapeptide product was placed in a 3,000 dalton cut-off dialysis tubing, dialyzed against water, and then verified by proton and C-13 nuclear magnetic resonance spectophotometry to be pure and to have a mean value for n greater than 40.

In order to impregnate the collagen analogue in preparation for compounding, strips (7 mm×25 mm) of DeBakey Elastic Dacron Fabric (USCI, a division of C. R. Bard, Inc., cat. No. 007830) were placed each on the bottom of a Teflon chamber of like dimension. Aqueous solutions containing 80 mg of PPP were added to each chamber covering the fabric. The temperature was raised and the coacervate allowd to settle into the Dacron weave largely filling the spaces between the fibers of the fabric. The supernatant was either removed or allowed to dry down to the level of the fabric strip. The PPP impregnated strips were then removed from the chambers and each was placed between 2.5 cm×2.5 cm glass slides separated by a Teflon spacer and the glass slides were sealed to prevent drying before and during irradiation.

The prepared samples were irradiated with gamma irradiation from a cobalt source as described in Example 1. The samples were placed in a cavity of a uniform radiation density of 13,317 roentgen per minute and left there for time periods allowing for 30, 40, 50 and 60 MRADs (i.e. $10^6$ radiation absorbed dose). The PPP coacervate was also irradiation cross-linked in the absence of a fabric using 4.4 mm ID glass tubes.

Stress-Strain measurements were made on all samples using the apparatus described in Example 1. As seen in FIG. 3A, using a different stress scale than for the remaining parts of the figure, the polypentapeptide (PPP), cross-linked at 30 MRAD is seen to exhibit a reasonable Young's (elastic) modulus during the initial elongation ($2.5 \times 10^6$ dynes/cm$^2$) but, due to rupture and flow of the strands coming sequentially into tension, the elastic modulus is quickly lost. Considering Dacron as an example of a collagen-analogue (see FIG. 2B, lower curves), the particular knit used in this study exhibits a rather modest elastic modulus during extension ($1.2 \times 10^6$ dynes/cm$^2$) which becomes even smaller during retraction (about $0.7 \times 10^6$ dynes/cm$^2$). Both were measured at a $\Delta L/L_i$ of 0.4. Irradiation of the Dacron alone was found to have no effect on its stress-strain properties. However, when the PPP is compounded to the Dacron by irradiation cross-linking, the product, PPP-Dacron, exhibits a very substantial elastic modulus both for the extension ($6 \times 10^6$ dynes/cm$^2$) and for the retraction ($4.3 \times 10^6$ dynes/cm$^2$) at 40% elongation as seen in FIG. 3B for the 50 MRAD sample. In FIG. 3C the curves for extension are compared for the 40, 50 and 60 MRAD samples. While there is not a large difference, it does appear that the 50 and 60 MRAD samples maintain a more consistent slope being displaced upward at lower elongations, crossing over to be displaced downward at higher elongations. The situation is analogous for the return to the relaxed length; the 50 and 60 MRAD samples achieve a somewhat better retraction and exhibit less hysteresis.

Some irradiation cross-linked samples were examined before and after stretching by means of a JEOL JSM U3 scanning electron microscope at 5 kV in the secondary electron emage mode using 200$\mu$ final aperture and a 0° stage tilt. Prior to examination the samples were attached to a carbon stub, coated with carbon, then aluminum to a thickness of about 200 Å (and/or Au-Pd) in a JEOL JEE-4C vacuum evaporator.

Figure 4B:
FIG. 4 shows a scanning electron micrograph of composite fibers of polypentapeptide and Dacron.
Figure 4A:
Figure 5:
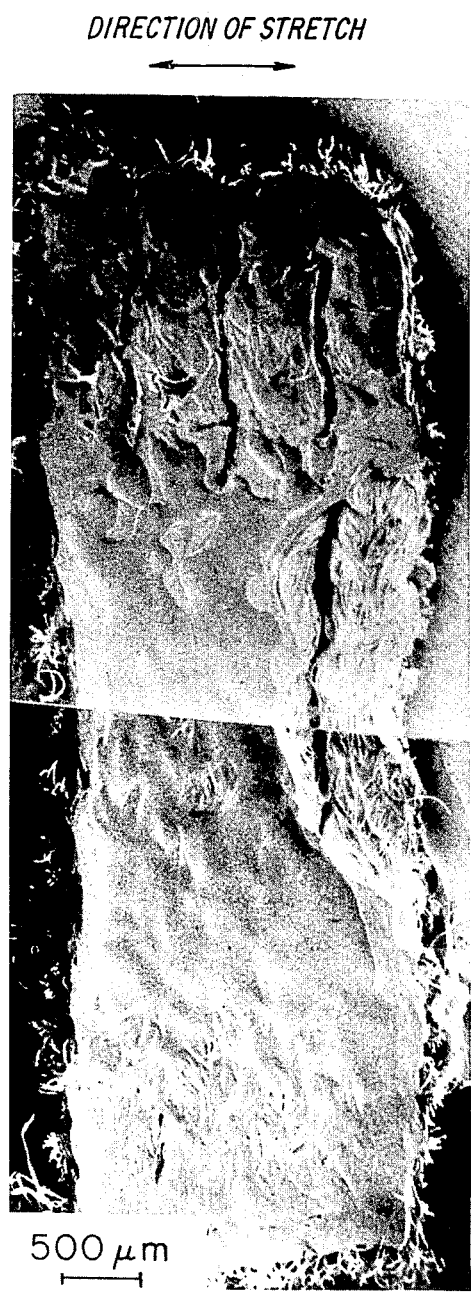
FIG. 5 shows a composite scanning electron micrograph of an entire fabric sample of the polypentapeptide/Dacron composite.
Figure 6A:
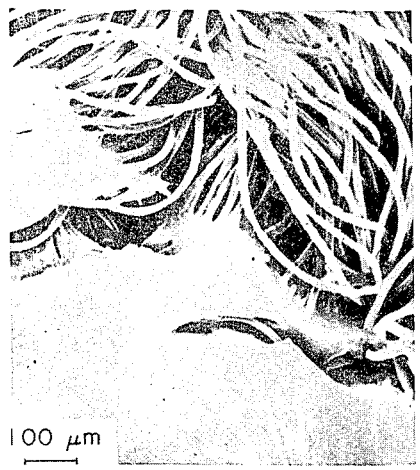
FIG. 6 shows higher magnification scanning electron micrographs of the composite fibers showing the bonding of the polypentapeptide to Dacron.
Figure 6B:
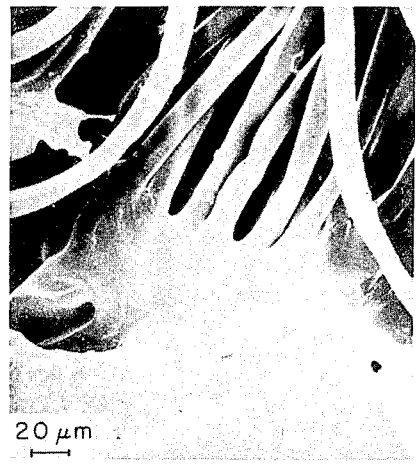
Figure 6C:
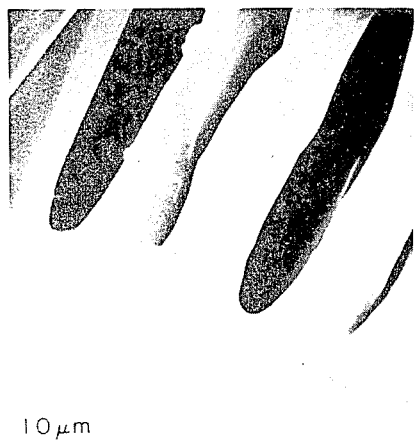
Figure 6D:

The extent of interaction of the PPP coacervate with the Dacron fibers is apparent in FIG. 4 which is unstretched PPP-Dacron (50 MRAD). For most fibers it is difficult to detect the junction between PPP and Dacron. This property could be anticipated from the highly glue-like, adhesive nature of the PPP coacervate which sticks to almost all materials with the exception of Teflon. The rough surface at the upper right hand corner of FIG. 4A is where the PPP was separated from the glass slide. A full width of the stretched 40 MRAD PPP-Dacron sample is seen in FIG. 5 which shows the effective embedding of the Dacron in the PPP. Evident in the micrograph are ruptures in the irradiation cross-linked PPP coacervate. These ruptures are at right angles to the direction of stretch and occur parallel to and at the edges of bands of woven Dacron fibers in this double knit fabric. The ruptures occur at sites in the weave where there is the largest displacement during stretching. Due to the remainder of the PPP permeating through the fabric and between the individual Dacron fibers, however, the elastomeric properties are retained but this aspect, which is a property of the weave, is likely responsible for the hysteresis seen in the stress-strain curves. In FIG. 6 is a closer look at a ruptured site which results from the uneven extension of the Dacron weave on stretching. It can be seen that the bonding of the PPP coacervate to Dacron fibers, as in this PPP-Dacron (60 MRAD) sample, is not disrupted. The adhesion of PPP to Dacron is well-retained in this ruptured area. At the highest level of magnification used, 5000×, a small crack can be found but this may be due to drying in the vacuum rather than due to rupturing on stretching.

As shown above, the compounding of PPP to Dacron provides strength to the PPP so that it can be cycled through numerous elongations and retractions with retention of the elastic properties. From the standpoint of the collagen analogue, the strength of the Dacron is retained while introducing a very substantial elastic modulus. As seen in FIGS. 4 and 6, the irradiation bonding of the PPP to the Dacron is such that one blends into the other as though a single material were present. This bonding appears to be well-retained after numerous extension relaxation cycles (see FIG. 5). The elastic modulus of PPP-Dacron ($\sim 6 \times 10^6$ dynes/cm$^2$) is greater than that reported for aortic fibrous elastin ($2.7 \times 10^6$ dynes/cm$^2$), due to the presence of the collagen analogue. The elastic modulus of PPP-Dacron is understandably greater than that of fibrous elastin and, in fact, approximates that of human aorta.

The hysteresis observed in FIGS. 3B, C and D is seen in Dacron alone and is likely due to the non-uniform extension of the PPP-Dacron leading to the ruptures observed in FIG. 5. In the regions of the weave where the extension is greater the cross-linked PPP ruptures such that retraction for this segment is largely left to the retraction exhibited by Dacron itself. It appears, therefore, that the desirable properties exhibited by compounding PPP to a collagen-analogue can be improved further by using a fabric with a more uniform extension.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. An elastomeric composite material comprising: an artificial core fiber, and
   an elastomeric polypeptide chemically bonded to the surface of said core fiber, wherein said polypeptide comprises tetrapeptide or pentapeptide repeating units or mixtures thereof, wherein said repeating units comprise amino acid residues selected from the group consisting of hydrophobic amino acid and glycine resisues and wherein said repeating units exist in a conformation having a $\beta$-turn, and the molecules of said elastomeric polypeptide are cross-linked by irradiating said polypeptide with ionizing radiation.

2. The elastomeric composite material of claim 1, wherein said hydrophobic amino acid residues are selected from the group consisting of hydrophobic α-amino acids.

3. The elastomeric composite material of claim 2 wherein said hydrophobic amino acid residues are selected from the group consisting of alanine, valine, leucine, isoleucine, proline, phenylalanine, tryptophan, and methionine.

4. The elastomeric composite material of claim 3, wherein the first amino acid residue of said repeating units is a residue of valine, leucine, or isoleucine.

5. The elastomeric composite material of claim 3 wherein the second amino acid residue of said repeating units is a residue of proline.

6. The elastomeric composite material of claim 3 wherein the third amino acid residue of said repeating units is a residue of glycine.

7. The elastomeric composite material of claim 3 wherein the fourth amino acid residue of said repeating units is a residue of tryptophan or glycine.

8. The elastomeric composite material of claim 1 wherein said tetrapeptide is Val-Pro-Gly-Gly.

9. The elastomeric composite material of claim 1 wherein said pentapeptide is Val-Pro-Gly-Val-Gly.

10. The elastomeric material of claim 1, wherein said core fiber has a tensile strength of at least 10 kg/mm$^2$.

11. The elastomeric composite material of claim 1, wherein the molecular weight of said polypeptide is at least 10,000 daltons.

12. The elastomeric composite fiber of claim 1, wherein the weight ratio of said core fiber to said polypeptide is from 10:1 to 1:10.

* * * * *